US010758183B2

(12) United States Patent
Lo et al.

(10) Patent No.: US 10,758,183 B2
(45) Date of Patent: Sep. 1, 2020

(54) PERSONALIZED SKIN ANALYSIS DEVICES

(71) Applicant: Cal-Comp Big Data, Inc., New Taipei (TW)

(72) Inventors: Teng-Nan Lo, New Taipei (TW); Ming-Hua Hung, New Taipei (TW)

(73) Assignee: Cal-Comp Big Data, Inc., New Taipei (TW)

( * ) Notice: Subject to any disclaimer, the term of this patent is extended or adjusted under 35 U.S.C. 154(b) by 560 days.

(21) Appl. No.: 15/397,704

(22) Filed: Jan. 3, 2017

(65) Prior Publication Data

US 2018/0184978 A1  Jul. 5, 2018

(51) Int. Cl.
*B25H 7/02* (2006.01)
*A61B 5/00* (2006.01)
*F16M 13/02* (2006.01)
*F16M 11/04* (2006.01)

(52) U.S. Cl.
CPC .......... *A61B 5/6832* (2013.01); *A61B 5/0015* (2013.01); *A61B 5/0077* (2013.01); *A61B 5/441* (2013.01); *B25H 7/02* (2013.01); *F16M 11/041* (2013.01); *F16M 13/02* (2013.01); *F16M 13/022* (2013.01)

(58) Field of Classification Search
None
See application file for complete search history.

(56) References Cited

U.S. PATENT DOCUMENTS 3,795,983 A    3/1974  Gallagher et al.
3,928,894 A *  12/1975 Bury ........................ B60R 1/04
                                                       24/304

6,520,463 B1 *  2/2003  Ouano ................. A47B 96/061
                                                      248/222.11
2005/0016122 A1 *  1/2005  Lai ....................... B65D 5/4229
                                                       52/749.1
2005/0210695 A1    9/2005  Muday et al.
(Continued)

FOREIGN PATENT DOCUMENTS

CN    203731052    7/2014
EP      2216582    8/2010
WO    2016061425   4/2016

OTHER PUBLICATIONS

Extended European Search Report for European Patent Application No. 18150070.3, dated Jun. 8, 2018.

*Primary Examiner* — Jeffry H Aftergut
*Assistant Examiner* — Jaeyun Lee
(74) *Attorney, Agent, or Firm* — Perkins Coie LLP

(57) ABSTRACT

The disclosed methods and systems can be used to install and configure a skin analysis device, for example. In one aspect, a system for installing a device onto a plane area is disclosed. The system comprises: an installation assistor comprising a reference mark for determining a position for installing the device; and a bracket for mounting the device. The bracket includes: at least one side substantially flat for affixing to the plane area; a sliding member extending from a side of the bracket that is opposite to the side for affixing to the plane area; and a raised member extending from the side of the bracket that is opposite to the side for affixing to the plane area, at a predetermined distance from the sliding member, wherein the raised member corresponds to a recessive portion of the device that is configured to lodge the raised member.

9 Claims, 13 Drawing Sheets

(56) References Cited

U.S. PATENT DOCUMENTS

| | | | |
|---|---|---|---|
| 2006/0186290 A1 | 8/2006 | Carnevali | |
| 2007/0295436 A1* | 12/2007 | Joseph | A47G 1/17 |
| | | | 156/60 |
| 2010/0012799 A1 | 1/2010 | Sexton | |
| 2013/0056598 A1* | 3/2013 | Ghiorghie | F16B 47/003 |
| | | | 248/205.3 |
| 2015/0070594 A1* | 3/2015 | Trachtenberg | H04N 5/64 |
| | | | 348/841 |

* cited by examiner

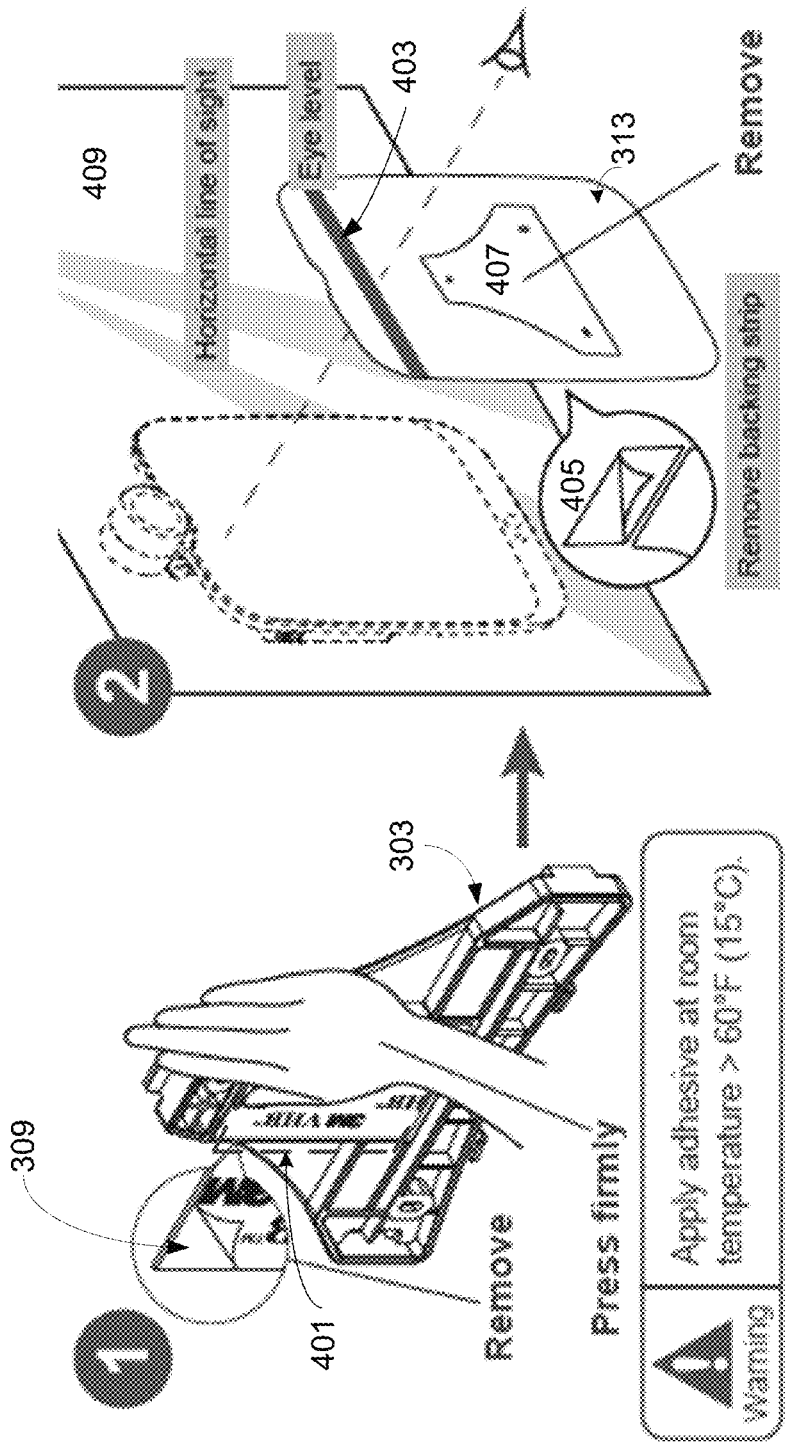

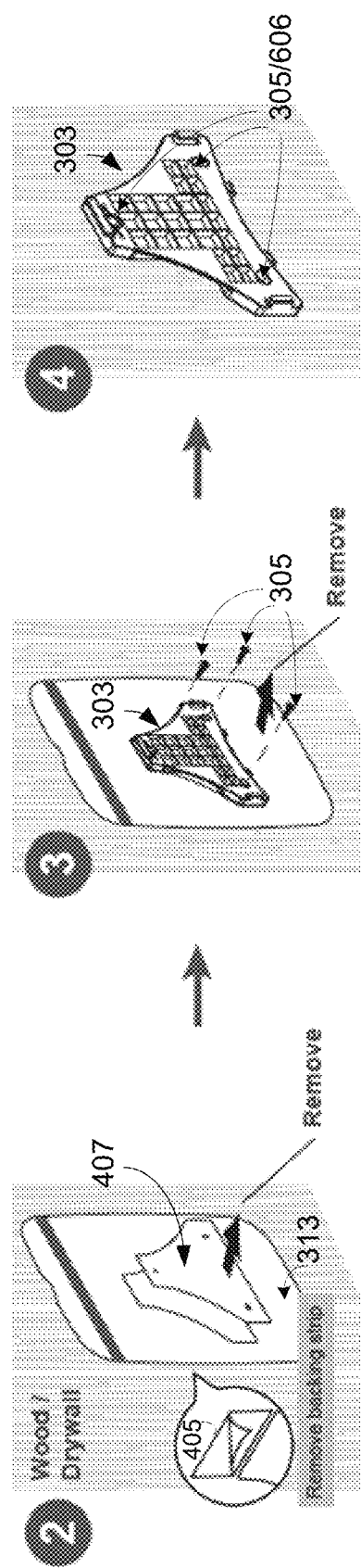

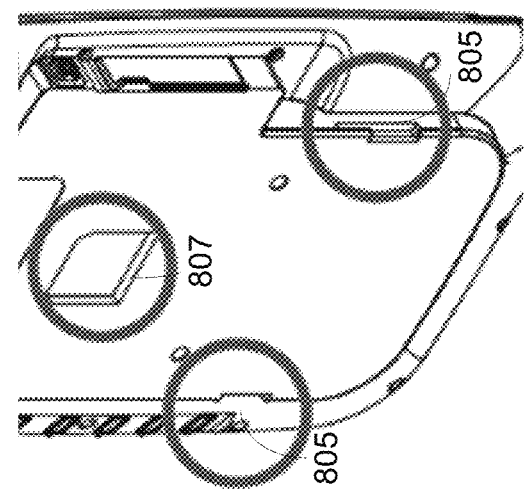
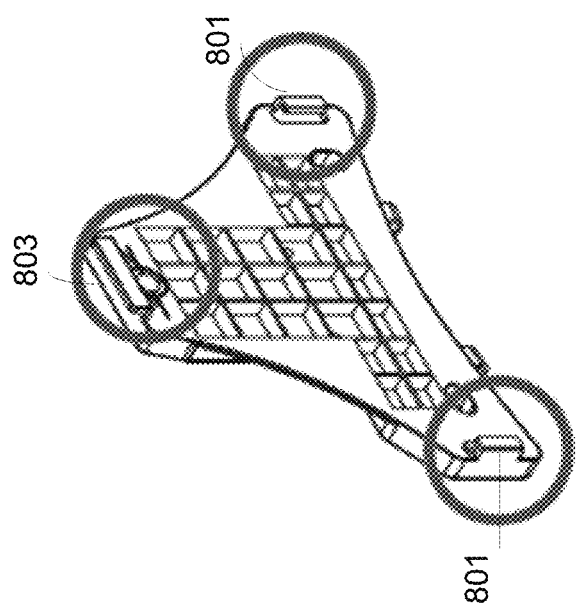
FIG. 8A

PERSONALIZED SKIN ANALYSIS DEVICES

CROSS REFERENCE TO RELATED APPLICATION

The entirety of the disclosure in U.S. patent application Ser. No. 15/397,700 entitled PERSONALIZED SKIN DIAGNOSIS AND SKINCARE is incorporated herein by reference as part of the disclosure of this application.

TECHNICAL FIELD

The subject matter disclosed herein relates to devices for performing personalized skin analysis and providing skin care feedback information based on the skin analysis.

BACKGROUND

In conventional skin diagnosis, a professional skin analysis apparatus is often involved to obtain information of skin conditions. To provide a final diagnosis, however, not only does it require a highly-trained professional (typically a dermatologist) to operate the apparatus, but it also entails his or her professional judgment on the skin analysis results rendered by the apparatus. Then, according to the diagnosis, the professional can recommend skin care products or treatments to the patients. To the general public, the conventional skin analysis apparatus is not readily accessible to install or operate.

SUMMARY

The disclosed technology described in this document provides devices for performing personalized skin analysis and related skin care feedback and includes the devices and methods for installing a skin analysis device for a user to perform skin diagnosis at home, office, or a chosen location, and to receive feedback or assistance in skin care or treatment. Yet, the subject matter disclosed herein is not limited to installing skin analysis devices, but also includes other devices that are intended to mount on a plane area such as a mirror or a wall.

In one aspect, a system for installing a device onto a plane area is disclosed. The system comprises: an installation assistor comprising a reference mark for determining a position for installing the device; and a bracket for mounting the device thereon. The bracket includes: at least one side substantially flat for affixing to the plane area; a sliding member extending from a side of the bracket that is opposite to the side for affixing to the plane area, wherein the sliding member corresponds to a groove portion of the device that is configured to guide the sliding member to slide to the base therein; and a raised member extending from the side of the bracket that is opposite to the side for affixing to the plane area, at a predetermined distance from the sliding member, wherein the raised member corresponds to a recessive portion of the device that is configured to lodge the raised member therein.

In another aspect, a method of installing a device onto a plane area is disclosed. The method comprises: disposing an installation assistor at a position of a plane area in reference to a mark on the installation assistor; affixing a substantially flat side of a bracket onto a region of the plane area that is defined by a template of the installation assistor corresponding to the bracket; and mounting the device onto the bracket by: guiding a sliding member of the bracket into a groove portion of the device to slide to the base therein, wherein the sliding member extends from a side of the bracket that is opposite to the side for affixing to the plane area; and lodging a raised member of the bracket to a recessive portion of the device for receiving the raised member therein, wherein the raised member extends from the side of the bracket that is opposite to the side for affixing to the plane area, at a predetermined distance from the sliding member.

In yet another aspect, a computer-implemented method of configuring a skin analysis device via a mobile device is disclosed. The computer-implemented method comprises: installing an application for conducting skin analysis and managing skin information on the mobile device; signing in the application using a user's account information; discovering, using the mobile device, a first wireless network broadcasted by the skin analysis device; and connecting the mobile device to the skin analysis device by directing the mobile device to join the first wireless network.

The above and other aspects and their implementations are described in greater detail in the drawings, the description and the claims

BRIEF DESCRIPTION OF THE DRAWINGS

FIGS. 4A-4D illustrate an exemplary process of installing the skin analysis device onto a mirror.

FIGS. 7A-7C illustrate an exemplary process of installing the skin analysis device onto a drywall.

FIG. 8A shows an exemplary structure of a bracket and a skin analysis device for mounting onto a plane area.

FIG. 8B illustrates an exemplary process for mounting the skin analysis device to the bracket and powering it on.

DETAILED DESCRIPTION

A person's skin condition significantly impacts a person's appearance and reflects a person's health. Accordingly, people invest a large amount of time and money on skin care products in the hope of gaining better-looking skin. Skin care is a significant industry with a global market of over $100 billion each year. Skin care awareness and consciousness are the driving forces behind this industry. Nowadays people are no longer content with multifunctional products and increasingly demand for more effective, better and more convenient tools to identify specific problems of their skin conditions and select proper skin care products that are specifically targeted at their unique skin conditions.

Professional skin analysis data is useful information to help people understand their skin conditions. However, to gain professional skin analysis data can be cumbersome as usually involving multiple trips to a dermatologist's office. In modern societies, people's busy schedules do not always allow easy access to such information. Moreover, it can be difficult to track and manage such professional analysis data for individuals. The systems and devices disclosed in this document can be implemented to assist people to easily understand, manage, and improve their skin conditions. Certain technical features of the disclosed technology are described in U.S. patent application Ser. No. 15/397,700 entitled PERSONALIZED SKIN DIAGNOSIS AND SKIN-CARE. The entirety of the disclosure in the aforementioned application is incorporated herein by reference as part of the disclosure of this application.

Figure 1A:
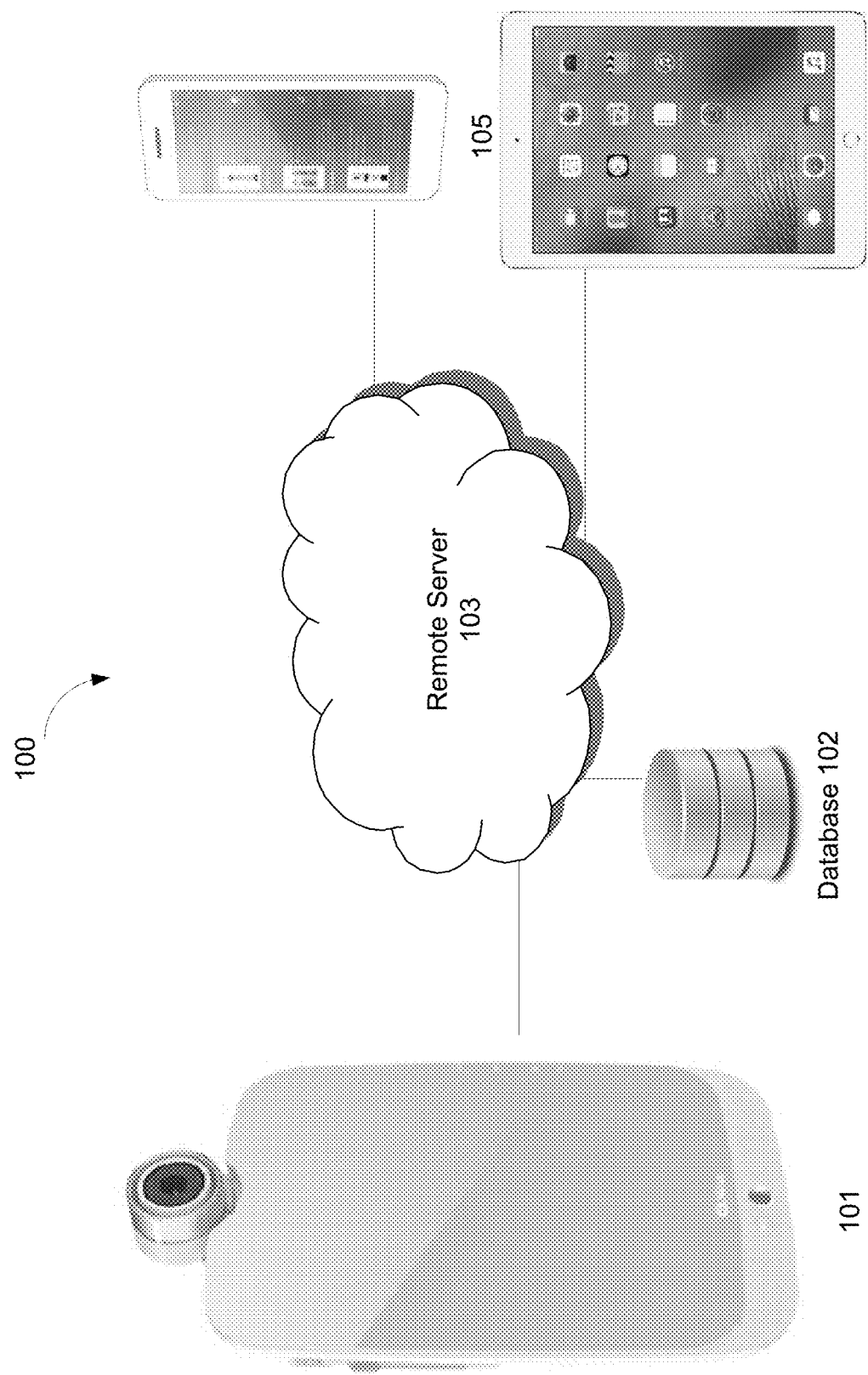
FIG. 1A shows an architecture overview of an exemplary skin analysis system.

Disclosed herein includes techniques, systems, and devices for installing skin analysis devices onto different types of plane areas or surfaces. FIG. 1A shows an architecture overview of an exemplary skin analysis system 100. A skin analysis device 101 can be set up in a user's bedroom or bathroom, for example. The device 101 is operative to display a graphical user interface for interacting with a user and conducting skin analysis. Alternatively, the display can be turned off and serve as a mirror to reflect a user's image. The skin analysis device 101 is in wireless communication to a remote server 103 (providing cloud services, for example) over the network to transmit and receive information, such as data corresponding to a user's skin profile, skin product recommendations, and skin tips. The information is stored over the network in a database 102 connected to the remote server 103. The database 102 and the remote server 103 allow the information to be displayed on the skin analysis device 101, as well as other portable devices, such as a mobile device 105 (e.g., a smartphone or a tablet).

Figure 1B:
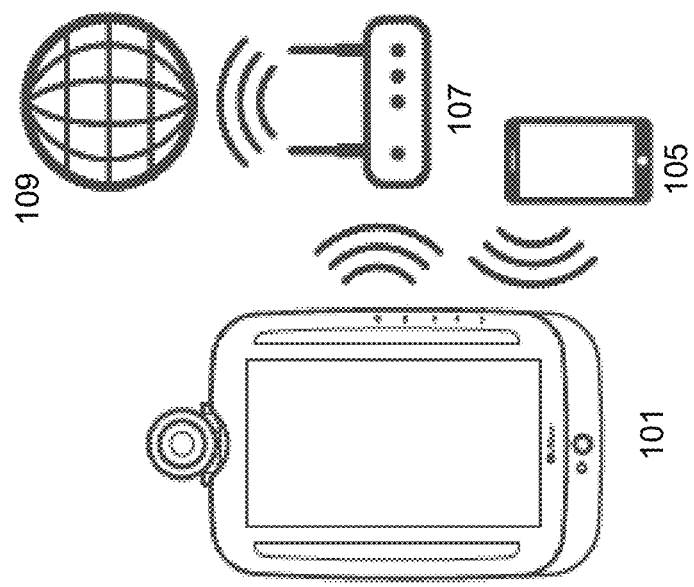
FIG. 1B shows an exemplary schematic diagram of the skin analysis device connecting with a wireless router and a mobile device.

In some embodiments, the skin analysis device 101 wirelessly communicates to the remote server 103 through a wireless router. FIG. 1B shows that, in order to enable wireless communication between the skin analysis device 103 and the network 109, the skin analysis device 101 is placed within the operating range of a local wireless network, such as that provided by a WiFi router 107. A mobile device 105 may be placed near the skin analysis device 101 for its initial setting up.

Figure 2A:
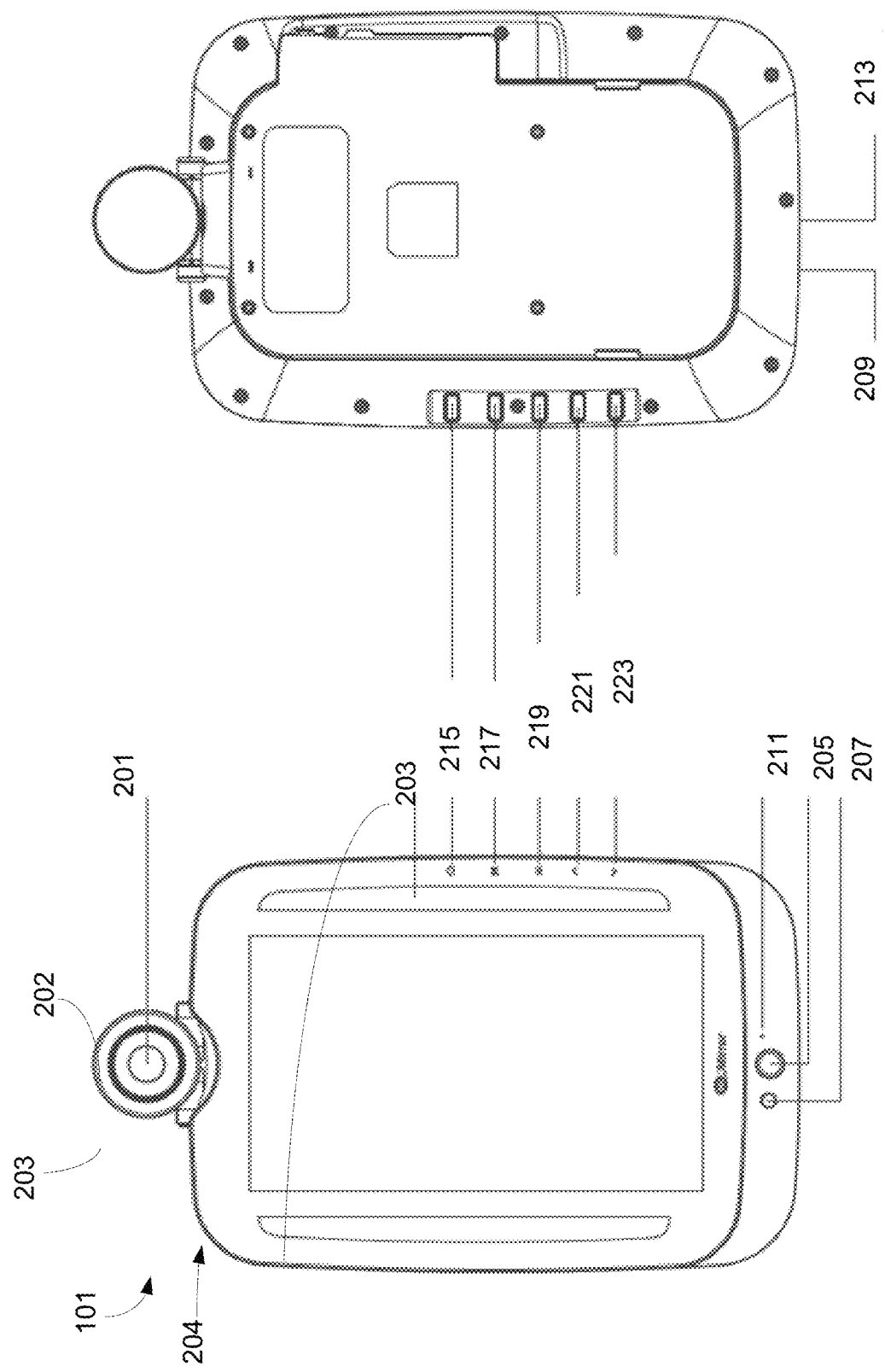
FIG. 2A shows an exemplary front and back view of the skin analysis device.

FIG. 2A shows an exemplary front and back view of the skin analysis device 101. The skin analysis device 101 includes a high-resolution camera module 201. The high-resolution camera module 201 includes a front cover 202 that is configured for manually closing by rotating a ring 203 coupled to the camera module 201. In some embodiments, when taking an image using the high-resolution camera module 201, the front cover 202 can be partially closed to exclude undesired background. To protect the user's privacy and/or to prevent an accidental image capturing, the front cover 202 can be closed entirely.

In some embodiments, two arrays of ambient make-up lights 203 are disposed at the reflective display 204 of the skin analysis device 101 to provide ambiance lighting. The device 101 also includes a variety of sensors as a part of the input interface, such as a motion sensor 205, an auto-wake-up sensor 207, and a temperature and humidity sensor 209. Moreover, the device 101 can include a microphone module 211 to capture voice input from the user, and a speaker module 213 to play media content.

The skin analysis device 101 can include several touch keys to provide shortcuts for the user to navigate the graphics user interface and operate the device 101. In some embodiments, the touch keys are provided at a side or the back of the device 101 as shown in FIG. 2A. The shortcuts include, for example: going directly to the home page (Home 215), turning on and off the display (Mirror 217), showing the settings menu (Menu 219), and navigating up and down on the current page (221 and 223).

Figure 2B:
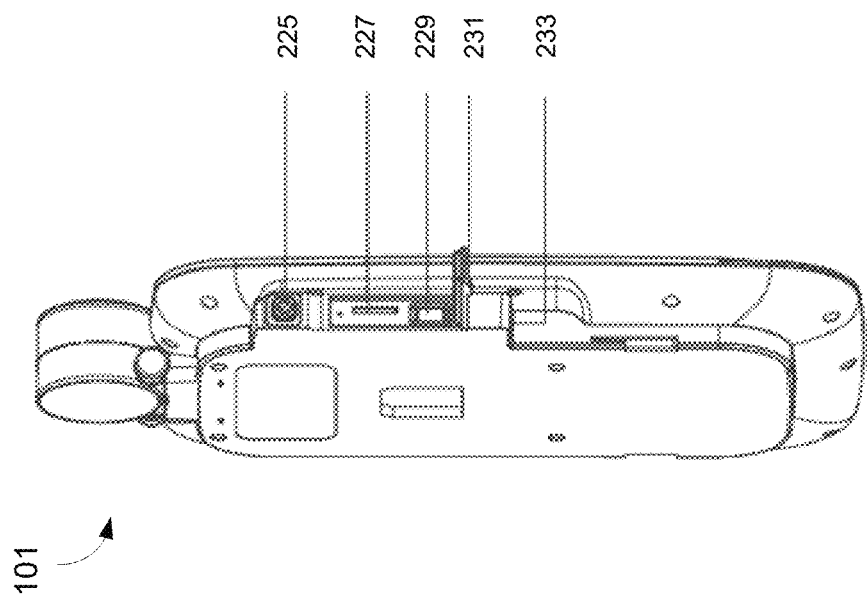
FIG. 2B shows an exemplary perspective view of the skin analysis device.

FIG. 2B shows an exemplary perspective view of the skin analysis device 101. This embodiment shows that the device 101 further includes a power button 225, a SD card slot 227 (for inserting a SD card to increase storage space for skin analysis images), a USB slot 229 (for connecting with peripheral devices), a waterproof cover 231 (for preventing water from the device 101, such as water splashes in a bathroom setting), and a power jack 233 (for receiving a power supply to charge the device 101).

Figure 3A:
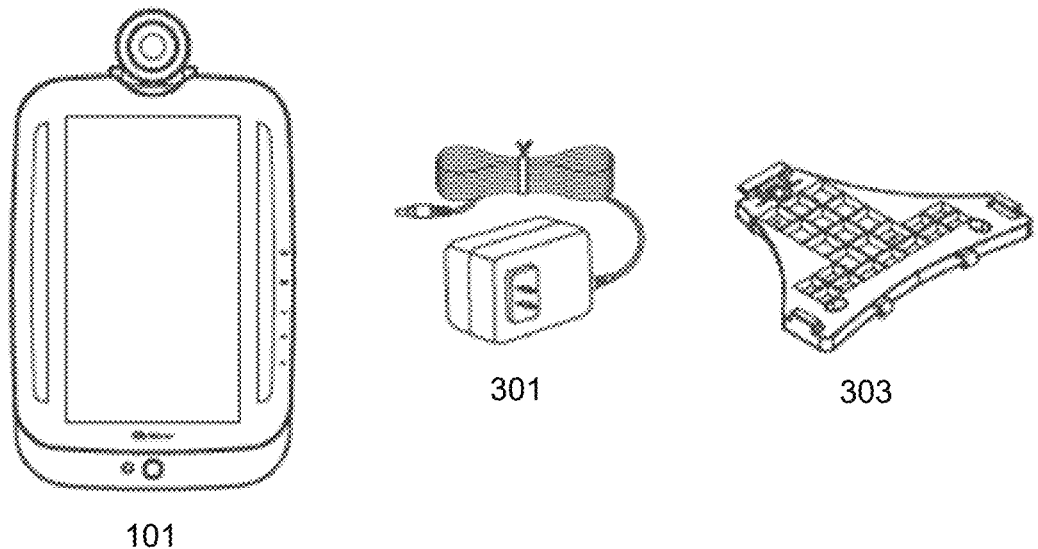
FIG. 3A shows an example of the skin analysis device, a power and a bracket for installing the skin analysis device.
Figure 3B:
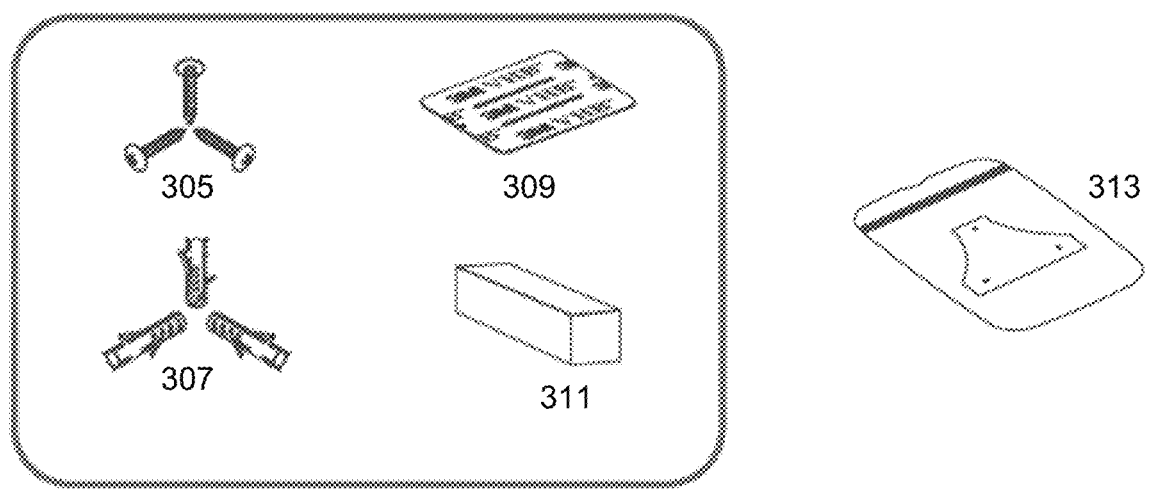
FIG. 3B shows exemplary accessories for installing the skin analysis device.

FIG. 3A shows exemplary components for installing the skin analysis device 101, including: a skin analysis device 101 to be installed, a power supply 301 to provide power to the skin analysis device 101, and an installation bracket 303 for mounting the skin analysis device 101 onto a plane area or surface, e.g., a mirror or a wall. FIG. 3B shows examples of additional accessories that facilitate installing the skin analysis device 101, including: a set of screws 305, a set of wall anchors 307, one or more adhesive tapes 309, a rubber pressing tool 311, and a cardboard assistor 313. How these accessories are used for installing the skin analysis device 101 is discussed in further detail in connection with FIGS. 4A-7C.

The skin analysis device 101 is designed to hang from a mirror, a wall, or other types of surfaces or plane areas. FIGS. 4A-7C show exemplary installation processes for installing the device 101 on a mirror, a concrete wall, and a drywall, respectively. Similar techniques can be applied to other types of surfaces or plane areas.

Figures 4C, 4D:
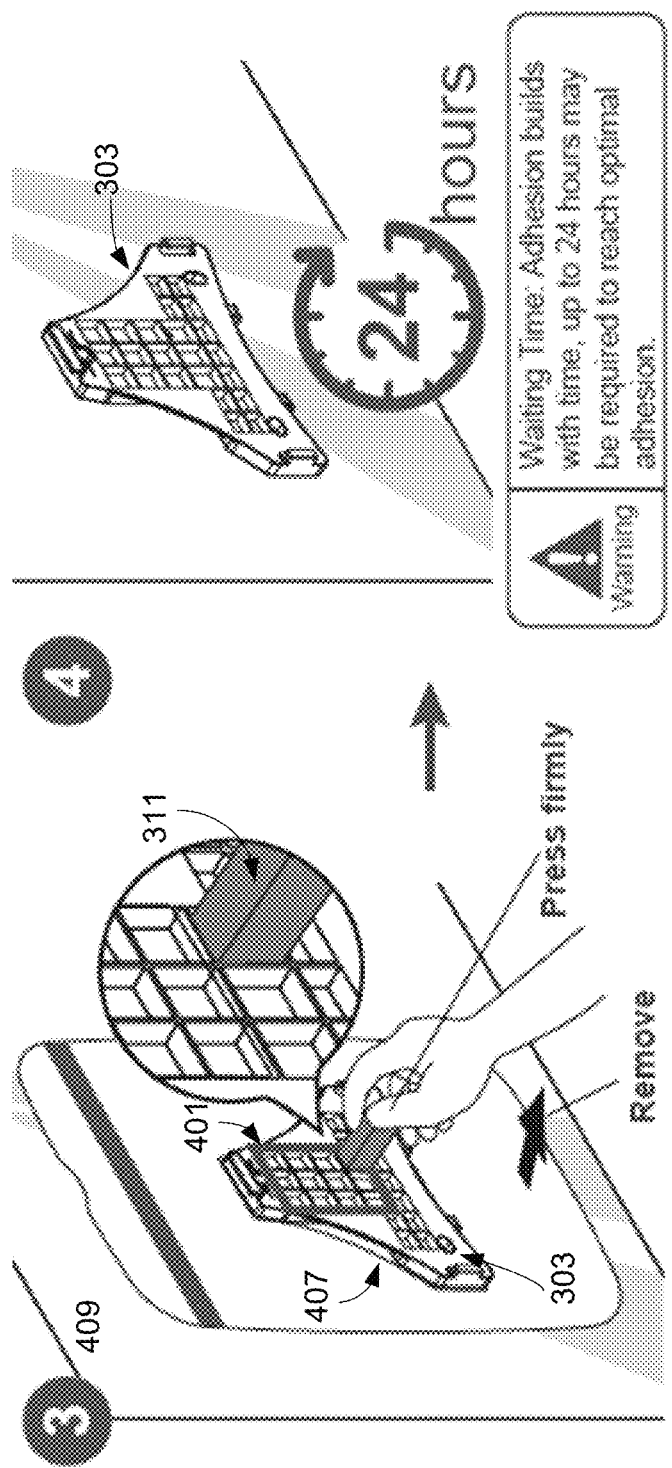

FIGS. 4A-4D demonstrate an exemplary installation process for installing the device 101 on a mirror. Referring to FIG. 4A, to install the skin analysis device 101 on a mirror, the adhesive tape 309 such as shown in FIG. 3B is applied by a user by removing a section of the backing from the adhesive tape 309 and attaching it to a rectangle area 401 of the bracket 303. Referring to FIG. 4B, the cardboard assistor 313 is disposed at a mirror 409 to determine a position on the mirror 409 the skin analysis device 101 should be mounted to. Specifically, the line 403 on the cardboard assistor 313 is suggested to be positioned at around the eye level of the user. The user then can remove the backing strip of the adhesive tape 405 on the cardboard assistor 313 and attach it to the mirror 409, at a location previously determined by reference to the line 403. In some embodiments, the cardboard assistor 313 includes a bracket template 407 that is detachable from the remaining areas of the cardboard assistor 313. In some implementations, the bracket template 407 is suggested to be removed before affixing the cardboard assistor 313 onto the mirror 409.

FIG. 4C illustrates that the remaining backing of the adhesive tape 309 is removed, and the bracket 303 is affixed onto the mirror 409 by the adhesive tape 309. More specifically, the bracket 303 is affixed to an area of the mirror 409 corresponding to the removed bracket template 407. The rubber pressing tool 311 (also shown in FIG. 3B) can be used to achieve a better adhesion effect by the adhesive tape 309. For instance, the rubber pressing tool 311 can be forced into each of the square cells of the bracket 303 and pressed firmly therein for a short duration of time (e.g., three seconds). In the particular embodiments shown in FIG. 4C, the bracket 303 includes twelve square or more cells 401. Then, as shown in FIG. 4D, the user can wait a period of time for the adhesive tape 309 to strengthen before mounting the skin analysis device 101 onto the bracket 303. In some implementations, the suggested wait time is 24 hours.

Figure 5:
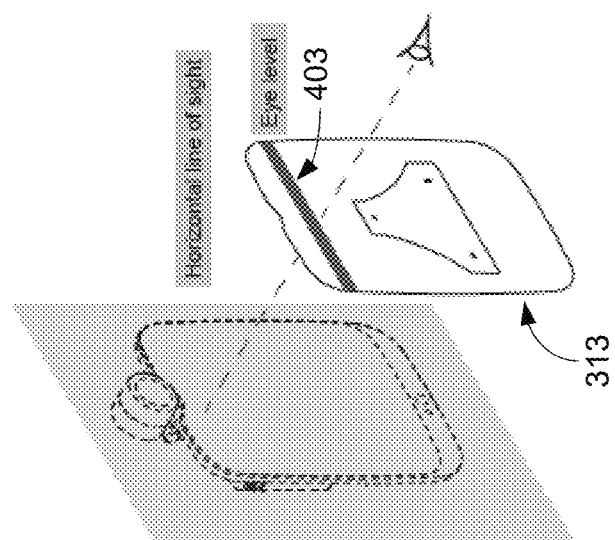
FIG. 5 illustrates an exemplary step to install the skin analysis device onto a wall.

Alternatively, the skin analysis device 101 can be installed on a wall. FIGS. 5-7C illustrate exemplary processes for installing the device 101 on a concrete wall and a drywall, respectively. FIG. 5 demonstrates that, similar to the installation process illustrated in FIG. 4B, the user can determine a proper position to install the skin analysis device 101 on the wall by aligning the line 403 on the cardboard assistor 313 at around the eye level of the user.

Figure 6C:
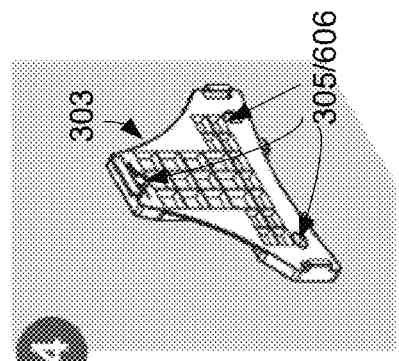
FIGS. 6A-6C illustrate an exemplary process of installing the skin analysis device onto a concrete wall.
Figure 6B:
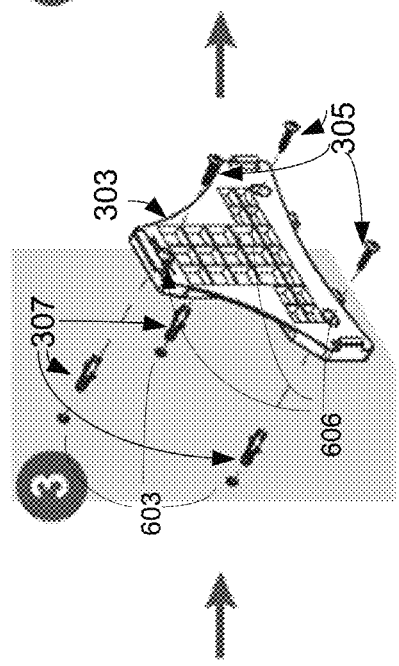
Figure 6A:
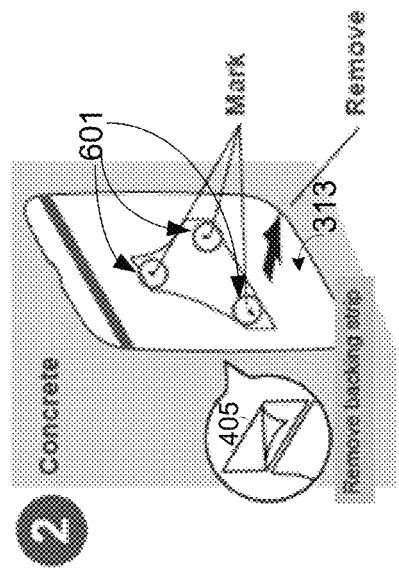

FIGS. 6A-6C demonstrate the remaining steps for installing the skin analysis device 101 on a concrete wall. In FIG. 6A, the user can use marks 601 on the cardboard assistor 313 to determine where on the wall to drill mounting holes 603 at. In some implementations, the user can first remove the backing strip 405 from the cardboard assistor 313 and temporarily affix it on the wall. This allows the user to mark on the wall for the mounting holes 603 more easily. After marking for the mounting holes 603, the cardboard assistor 313 can be removed from the wall in its entirety. The user then can drill the mounting holes 603 based on the marks (not shown) on the wall. After drilling the mounting holes 603 on the wall, the user can place the wall anchors 307 (also shown in FIG. 3B) into the mounting holes 603. Then the user can hold the bracket to align drill holes 606 formed thereof with the anchors 307 on the wall, and screw the bracket 303 onto the wall using the set of screws 305 (also shown in FIG. 3B), as demonstrated in FIG. 6B. Referring to FIG. 6C, the bracket 303 affixed to the wall by the screws 305 through the drill holes 606 is illustrated. Fastening hardware other than screws such as nails, fasteners, and bolts/nuts or the like can be used for affixing the bracket 303.

FIGS. 7A-7C demonstrate a process for installing the skin analysis device 101 onto a drywall, which is similar to that illustrated in FIGS. 6A-6C. Referring to FIG. 7A, the bracket template 407 can be removed from the cardboard assistor 313. In some implementations, the user can remove the backing strip 405 from the adhesive tape on the cardboard assistor 313 and temporarily affix the cardboard assistor 313 on the drywall. FIG. 7B shows that the bracket 303 is placed onto an area of the wall corresponding to the removed bracket template 407. FIG. 7C shows that the bracket 303 is affixed onto the drywall using the set of screws 305 through the drill holes 606. The cardboard assistor 313 can then be removed from the drywall, as shown in FIG. 7C.

Figure 8B:
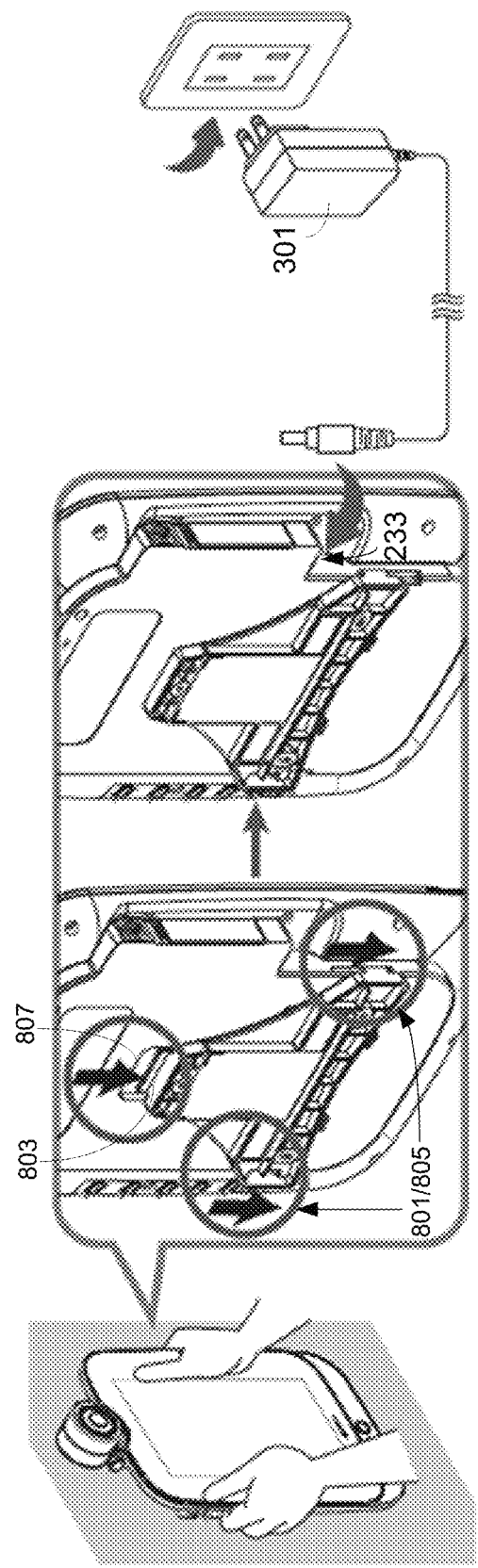

After the bracket 303 is secured onto a plane area (such as a mirror, a wall, or another type of surface as described above), the skin analysis device 101 can be mounted to the bracket 303. FIG. 8A shows that, in some embodiments, the bracket 803 includes two sliders 801 and one mounting tab 803. The two sliders 801 extend from the two lower corners of the bracket 303, the locations of which correspond to two grooves 805 formed in the back of the skin analysis device 101 for receiving the sliders. The mounting tab 803 extends from an upper corner of the bracket 303, the location of which corresponds to a recessive portion 807 formed in the back of the skin analysis device 101. The sliders 801, mounting tab 803, grooves 805 and recessive portion 807 allow the bracket 303 and the skin analysis device 101 to couple together securely. FIG. 8B shows that, to mount the skin analysis device 101 onto the bracket 303, the user can hold the skin analysis device 101 firmly with both hands and guide the sliders 801 down to the base of the grooves 805 such that the sliders 801 are lodged therein, while placing the mounting tab 803 into the recessive portion 807 to secure to the bracket 303. Then the user can connect the skin analysis device 101 to a power source using the power supply 301 (also shown in FIG. 3A) via the power jack 233 (also shown in FIG. 2B).

Figure 9:
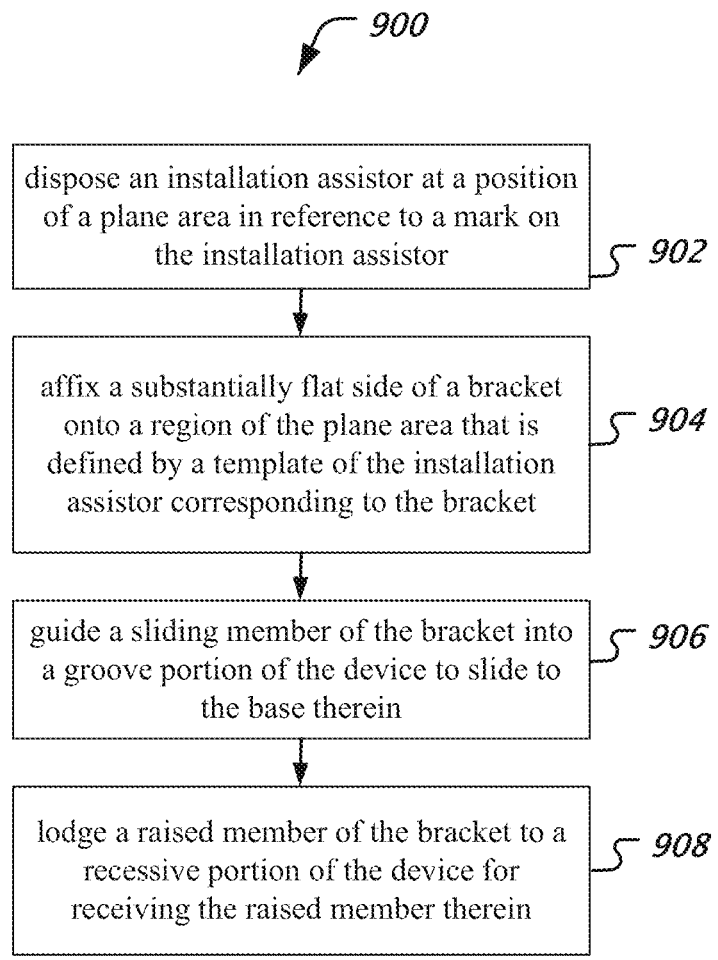
FIG. 9 is a flowchart of an exemplary method for installing a skin analysis device.

FIG. 9 shows an exemplary flowchart of a method 900 of installing a skin analysis device. The method 900 includes, at 902, disposing an installation assistor at a position of a plane area in reference to a mark provided on the installation assistor, such that the mark is disposed at the eye level of a user; at 904, affixing a substantially flat side of a bracket onto a region of the plane area that is defined by a template of the installation assistor corresponding to the bracket; at 906, mounting the device onto the bracket by guiding a sliding member of the bracket into a groove portion of the device to slide to the base therein, wherein the sliding member extends from a side of the bracket that is opposite to the side for affixing to the plane area; and, at 908, mounting the device onto the bracket by lodging a raised member of the bracket to a recessive portion of the device for receiving the raised member therein, wherein the raised member extends from the side of the bracket that is opposite to the side for affixing to the plane area, at a predetermined distance from the sliding member.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for installing a device onto a plane area, comprising:
    an installation assistor comprising a reference mark to be placed on the plane area for marking a position for installing the device on the plane area, the installation assistor including a bracket template located at a center area surrounded by a remaining area of the installation assistor, the bracket template detachable from the remaining area of the installation assistor; and
    a bracket for mounting the device onto the plane area by using the reference mark and configured attachable to a portion of the plane area that corresponds to a location of the bracket template detached from the installation assistor, the bracket having two lower corners and an upper corer and comprising:

at least one side substantially flat for affixing to the portion of the plane area relative to the reference mark;

a sliding member disposed at one of the two lower corners of the bracket and extending from a side of the bracket that is opposite to the at least one side for affixing to the plane area, wherein the sliding member corresponds to a groove portion of the device that is configured to guide the sliding member to slide relative to the device and located on a back side of a portion of the device and along a boundary of the portion of the device, the back side opposite to a front side of the device to display data; and a raised member disposed at the upper corner of the bracket and extending from the side of the bracket that is opposite to the at least one side for affixing to the plane area, the raised member located at a predetermined distance from the sliding member, wherein the raised member corresponds to a recessive portion of the device that is configured to lodge the raised member and located on the back side of the portion of the device, wherein the recessive portion of the device located closer to a center of the back side of the portion of the device than the sliding member.

2. The system of claim 1, wherein the installation assistor comprises a cardboard.

3. The system of claim 1, wherein the bracket comprises a second sliding member disposed at the side of the bracket that is opposite to the side for affixing to the plane area, wherein the second sliding member corresponds to a second groove portion of the device that is configured to guide the second sliding member to slide, and wherein the second sliding member is located at the other lower corner of the bracket.

4. The system of claim 1, wherein the bracket comprises a plurality of drill holes for receiving fastening hardware to affix the bracket onto the plane area.

5. The system of claim 4, wherein the installation assistor includes marks thereon to indicate locations of the plurality of drill holes in the bracket, respectively, for mounting on the plane area.

6. The system of claim 4, wherein the fastening hardware includes a plurality of screws.

7. The system of claim 1, wherein the bracket comprises a plurality of integral cells disposed at the side of the bracket that is opposite to the side for affixing to the plane area, wherein the plurality of integral cells are each configured to receive a columnar pressing tool for pressing the bracket against the plane area.

8. The system of claim 1, further comprising an adhesive material applicable to the bracket and installation assistor for adhering to the plane area.

9. The system of claim 8, wherein the adhesive material includes an adhesive tape.

* * * * *